United States Patent [19]

Butera et al.

[11] Patent Number: 4,994,459

[45] Date of Patent: Feb. 19, 1991

[54] ARYLOXYPROPANE SUBSTITUTED PIPERAZINE DERIVATIVES WITH ANTIARRHYTHMIC AND ANTIFIBRILLATORY ACTIVITY

[75] Inventors: John A. Butera, Kendall Park; Jehan F. Bagli, Princeton, both of N.J.

[73] Assignee: American Home Products Corporation, New York, N.Y.

[21] Appl. No.: 449,273

[22] Filed: Dec. 11, 1989

[51] Int. Cl.$^5$ .................. A61K 31/495; C07D 403/04
[52] U.S. Cl. ..................................... 514/252; 514/254; 544/295; 544/360; 544/368; 544/370
[58] Field of Search .............. 544/295, 360, 368, 370; 514/252, 254

[56] References Cited

U.S. PATENT DOCUMENTS

| | | | |
|---|---|---|---|
| 4,591,590 | 5/1986 | Ueda et al. | 544/360 |
| 4,616,017 | 10/1986 | Baldwin et al. | 544/360 |
| 4,806,536 | 2/1989 | Cross et al. | 544/370 |

FOREIGN PATENT DOCUMENTS

| | | |
|---|---|---|
| 0233051 | 6/1987 | European Pat. Off. . |
| 0269985 | 6/1988 | European Pat. Off. . |

*Primary Examiner*—Glennon H. Hollrah
*Assistant Examiner*—James H. Turnipseed
*Attorney, Agent, or Firm*—Walter Patton

[57] ABSTRACT

This invention relates to certain substituted piperazines possessing anti-arrhythmic activity, to pharmaceutical compositions and to methods for production thereof.

9 Claims, No Drawings

ARYLOXYPROPANE SUBSTITUTED PIPERAZINE DERIVATIVES WITH ANTIARRHYTHMIC AND ANTIFIBRILLATORY ACTIVITY

BACKGROUND OF THE INVENTION

Class III antiarrhythmic agents may be categorized as having the ability to markedly prolong Purkinje fiber action potential duration without producing significant changes in maximal upstroke velocity. Unlike Class I antiarrhythmic agents, a pure Class III agent displays no effect on cardiac sodium channels. The electrophysiologic properties of a compound possessing a Class III activity profile are observed in vivo as negligible effects on atrial, ventricular and H-V conduction times while producing a marked increase (greater than 20 percent) in both the atrial and ventricular refractory period. In contrast, Class I agents will demonstrate a marked slowing of ventricular conduction velocity, with variable effects on the refractory period. Recent reviews of these agents are by: Brexton et al., Pharmac. Ther. 17, 315–55 (1982); Vaughan-Williams, J. Clin. Pharmacol. 24, 129–47 (1984); Steinberg et al., Ann. Rep. Med. Chem. 21, 95–108 (1986).

The following workers have reported the selective Class III antiarrhythmic activity of the dextro enantiomer of 4-(2-isopropylamino-1-hydroxyethyl)-methanesulfonamide (MJ-1999, Sotalol): Taggart, et al., Clin. Sci. 69, 631–636 (1985) and McComb, et al., J. Am. Coll. Cardiol. 5, 438 (1985).

Silberg et al., ACAD Rep. Populace Romire, Fillala Clug, Studee Cercetari Med., 10244–52 (1959) disclose p-acetylamino-N-(2-diethylaminoethyl)benzenesulfonamide and compare its antiarrhythmic properties with procainamide.

Wohl et al. disclose N-[2-(diethylamino)ethyl]-4-[(methylsulfonyl)amino]-benzamide hydrochloride as a potential class III antiarrhythmic agent in U.S. Pat. No. 4,544,654, Oct. 1, 1985.

Cross et al. have reported various (phenyl(carbonyl)alkyl)-4-(pyridinyl or imidazolyl)piperazines as useful antiarrhythmic agents in European Patent 0233051, June 19, 1987. A series of phenylpiperazinyl-propranol derivatives are disclosed in U.S. Pat. 4,428,950 by Franke et al., however, the antiarrhythmic activity (if any) is not discussed.

DESCRIPTION OF THE INVENTION

In accordance with this invention, there is provided a group of antiarrhythmic agents classified by their pharmacological profile as Class III antiarrhythmic agents of the formula (I)

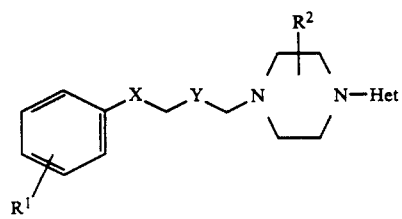

wherein $R^1$ is alkylsulfonamido of 1 to 6 carbons, arylsulfonamido of 6 to 10 carbons, perfluoroalkylsulfonamido of 1 to 6 carbon atoms, alkylsulfone or alkylsulfoxide of 1 to 6 carbon atoms, $NO_2$, CN, or 1-imidazolyl; $R^2$ is hydrogen or straight or branched alkyl chain of 1 to 6 carbon atoms; X is O, S, or $NR^3$ wherein $R^3$ is H or a straight or branched alkyl chain of 1 to 6 carbon atoms; Y is $CH_2$ or CHOH; Het is selected from the group consisting of

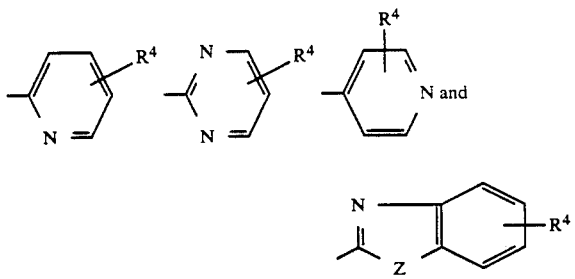

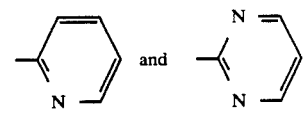

wherein $R^4$ is H, $-NHSO_2$ ($C_1$ to $C_6$ alkyl) or $NO_2$; Z is O, S, $NR^5$ wherein $R^5$ is H or alkyl of 1 to 6 carbon atoms and the pharmaceutically acceptable salts thereof.

The preferred compounds of the present invention are of formula (II)

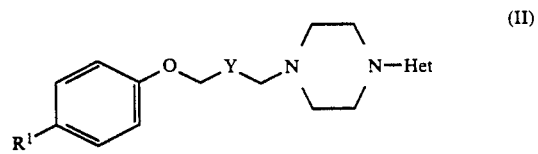

wherein $R^1$ is methylsulfonamido, or nitro; Y is $CH_2$ or CHOH; Het is selected from the group consisting of and the pharmaceutically acceptable salts thereof.

The preferred compounds of the present invention are

α-[(4-nitrophenoxy)methyl]-4-(2-pyridinyl)-1-piperazineethanol;

N-[4-[2-hydroxy-3-[4(2-piperazinyl]propoxy]phenyl]-methanesulfonamide;

N-[4-[2-hydroxy-3-[4-(2-pyrimidinyl)-1-piperazinyl]-propoxy]phenyl]methanesulfonamide;

(S)-α-[(4-nitrophenoxy)methyl]-4-(2-pyridinyl)-1-piperazineethanol;

(R)-α-[(4-nitrophenoxy)methyl]-4-(2-pyridinyl)-1-piperazineethanol;

and the pharmaceutically acceptable salts thereof.

It is to be understood that the definition of the compounds of Formula (I) encompasses all possible stereoisomers and mixtures thereof which possess the activity discussed below. In particular, it encompasses racemic modifications and any optical isomers which possess the indicated activity.

The pharmaceutically acceptable salts of the antiarrhythmic agents of this invention are prepared directly by neutralization of the free base. These physiologically acceptable salts may be formed with organic or inorganic acids, such as hydrochloric, hydrobromic, phosphoric, sulfuric, sulfamic, nitric, methylsulfonic, acetic, maleic, succinic, fumaric, tartaric, citric, salicylic, lactic, napthalenesulfonic acid and the like.

The compounds of this invention of formula (I) wherein Y is CHOH may be prepared by reaction of an appropriately substituted epoxide of formula (III)

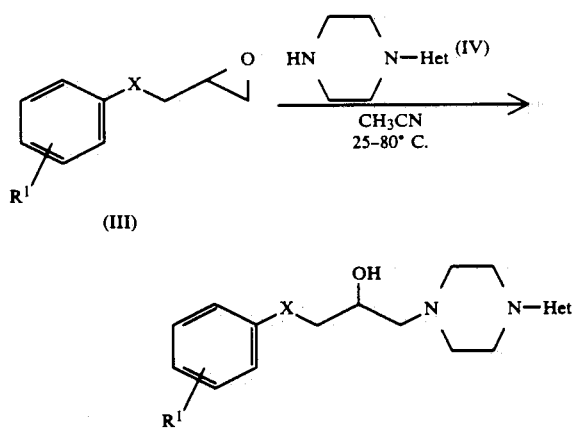

wherein $R^1$ and X are as defined above with the required N-substituted piperazinyl moiety of formula (IV) wherein Het is as defined above in solvents such as acetone or acetonitrile. The latter may in turn be prepared from a halo-substituted heterocycle and a suitably protected derivative of piperazine.

When Y is $CH_2$, the compounds of formula (I) can be prepared by the reaction of an appropriately substituted aryl compound of formula (V)

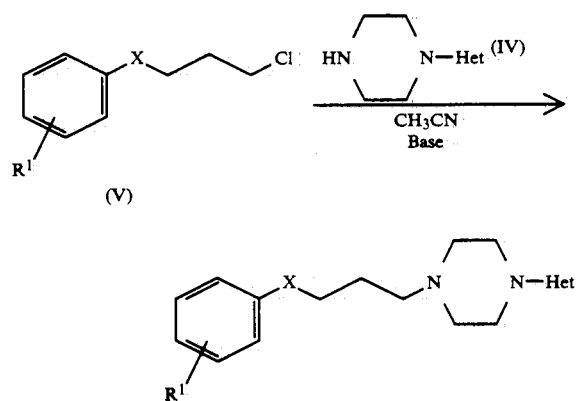

wherein $R^1$ and X are as defined above with the required N-substituted piperazinyl moiety of formula (IV) wherein Het is as defined above in the presence of a suitable base in solvents such as acetone or acetonitrile. These reactants are generally known compounds and otherwise are routinely prepared by techniques well within the skill of the chemist.

CORONARY OCCLUSION—REPERFUSION

The compounds of this investigation demonstrate antiarrhythmic activity when tested in the standard experimental animal in accordance with the following procedure.

Pigs (Durrock-Landrace cross) of either sex weighing 12 to 24 kg were anesthetized by administration of sodium pentobarbital. (35 mg/kg i.p. and supplemented with 5 mg/kg/hr. i.v.) and ventilated with room air following tracheotomy (minute volume: 200 mL/kg). The left femoral artery and vein were cannulated for the recording of blood pressure and for drug administration, respectively. Blood pressure and lead II EKG were recorded on a chart recorder.

The heart was exposed by a left thoracotomy performed at the fifth intercostal space. A silk ligature was placed beneath the left anterior descending coronary artery (LAD) about 1.5 cm from its origin and distal to the septal artery branch. The artery was occluded by lifting the vessel with the ligature and quickly placing a bull-dog clamp (3×12 mm padded jaws) over the artery. The clamp remained in place for a period of 20 minutes. Removal of the clamp produced a rapid reperfusion of the ischemic myocardium as evidenced by the return of normal color to the myocardium distal to the site of occlusion. Ectopic activity was monitored during occlusion and reperfusion by recording the lead II EKG at chart speeds of 5 to 25 mm/second. Animals were allowed to stabilize for at least 30 minutes prior to drug administration.

Pigs were randomized into groups receiving either vehicle or test drug at a given dose (1–5 mg/kg i.v.) 20 minutes before LAD occlusion. Animals surviving the period of occlusion were subsequently reperfused. No attempt was made to resuscitate animals experiencing ventricular fibrillation (VF) at any time following occlusion. In the absence of treatment, less than 30 percent of the animals survive the 20 minute period of occlusion, with a mean time to death onset of 8 to 12 minutes. Effective compounds either prevent death due to VF or prolong survival time.

Fraction of pigs surviving occlusion and reperfusion:

|  | Vehicle | Cmpd 1 2.5 mg/Kg | Cmpd 1 5 mg/Kg |
|---|---|---|---|
| 20 min. occlusion | 0/4 | 1/4 | 4/4 |
| Reperfusion | — | 0/4 | 2/4 |

CARDIAC ELECTROPHYSIOLOGY

The compounds of this invention display a Class III antiarrhythmic profile. The Class III antiarrhythmic activity was established in vitro and in vivo in accordance with the following standard test procedures.

In Vitro:

Bundles of free-running Purkinje fibers with attached myocardium obtained from either ventricle of adult dog heart were pinned without stretching to the bottom of a 10 mL tissue chamber and continuously superfused with oxygenated Tyrode's solution at a flow rate of 5 mL/min. The composition of the Tyrode's solution was (mM): NaCl, 138; KCl 4; $CaCl_2$, 2; $MgCl_2$ 0.5; $NaHCO_3$, 24; dextrose, 5.5. The solution was aerated with 95% $O_2$–5% $CO_2$ at 37° C. Bath temperature was maintained at 37±0.5° C. by circulating the pre-warmed superfusate through a thermostatically controlled water bath immediately prior to entering the tissue chamber.

The preparations were stimulated through bipolar Teflon-coated silver wires, bared at the tips, placed on the endocardial surface of the attached myocardium, using a digital stimulator set to deliver constant current pulses 1.5-msec in duration at cycle lengths of 300 or 1000 msec. Stimulus strength was set at approximately 2×diastolic threshold, and adjusted as required throughout the experiment. All preparations were allowed to equilibrate in the tissue chamber for at least 1 hour before measurements were begun. Subsequently, a minimum of 60 minutes were allowed for equilibration with each drug-containing superfusate before post-drug measurements were made. Impalements were made at 6 to 10 sites throughout the preparation before and after drug exposure. Offset potentials were rechecked after each impalement.

Glass microelectrodes filled with 3M KCl were coupled to high impedance negative capacitance electrometers and Ag/AgCl half-cells used as reference electrodes. The first derivative of the action potential upstroke ($V_{max}$) was obtained using an analog differentiator circuit, coupled to a peak-hold circuit that retained the recorded value of $V_{max}$ for 30 to 70-msec. Action potential and $V_{max}$ tracings were displayed on a storage oscilloscope, and photographed for later analysis. In addition, chart paper recordings of Vmax were obtained using the peak-hold device output.

Fresh stock solutions of drug were prepared for each experiment. Compounds were dissolved in distilled water at total concentrations of 1 to 10 mg/mL, and subsequently diluted to a final concentration of 3 to 10 $\mu$M in appropriate volumes of normal Tyrode's solution for evaluation.

Action potential (AP) parameters measured included: diastolic take-off potential or activation voltage, ($V_{act}$); AP overshoot ($V_{os}$); AP duration measured as the time taken to repolarize to $-20$ mV ($APD_{-20}$), $-60$ mV ($APD_{-60}$), and $-80$ mV ($APD_{-80}$); and maximal upstroke velocity ($V_{max}$). An increase in $APD_{-60}$ that occurred without a significant change in $V_{max}$ was taken, by definition, to indicate Class III antiarrhythmic activity "in vitro".

In Vitro:

Mongrel dogs of both sexes weighing 12 to 18 kg were anesthetized with sodium pentobarbital (35 mg/kg i.v. supplemented with 5 mg/kg/h) and artificially ventilated with room air (minute volume: 200 mL/kg).

The heart was exposed by a right thoracotomy performed at the fifth intercostal space and suspended in a pericardial cradle. Epicardial electrodes for stimulation and recording were sutured to the free wall of the lower right atrium and near the base of the right ventricle. Each electrode set contained a linear array of electrodes consisting of 1 bipolar stimulating electrode and 2 bipolar recording electrodes embedded in a rigid acrylic matrix. The stimulating bipole was 7 mm from the proximal recording electrode, which in turn was 10 mm from the distal recording bipole. Each electrode array was oriented to be parallel to the epicardial fiber axis.

Arterial blood pressure and lead II ECG were displayed on a chart recorder and monitored on an oscilloscope. Conduction times and refractory periods were measured during pacing at a cycle length of 300 msec. The dog heart was paced by a stimulator driving a constant current isolation unit. Electrical signals from the atrial and ventricular electrodes were displayed on a digital oscilloscope and recorded by a ink-jet recorder. Diastolic threshold was determined before and after each trial.

Refractory periods of the right atrium and right ventricle (AERP and VERP) were determined by introducing an extrastimulus ($S_2$) every 8 paced beats ($S_1$). The extrastimulus was followed by a 4-second rest interval during which no pacing occurred. Both $S_1$ and $S_2$ were of identical intensity (twice threshold) and duration (2 msec). The $S_1$-$S_2$ interval was gradually decreased in 2-msec steps until the extra-stimulus failed to induce a propagated response. This $S_1$-$S_2$ interval was considered to define effective refractory period.

Atrial and ventricular (ACT and VCT) conduction times were measured as the time interval between the 2 electrograms recorded at the proximal and distal sites of the recording electrode array. The time of activation for electrograms with predominantly biphasic complexes was taken as the moment when the trace crossed the zero reference line, and for triphasic complexes, as the peak of the major deflection.

Animals received the test compound by i.v. injection. Drugs were administered cumulatively at the following dose levels: 1, 2.5, 5, 7.5, 10 mg/kg. Each dose was administered over a 3 minute period. Electrophysiologic testing was performed 15 minutes following the end of dosing. Every 30 minutes the dog received the next incremental dose.

Vehicle-treated animals did not show any significant change of the electrophysiologic parameters. An increase in ERP that occurred without a significant decrease of CT was taken, by definition to indicate "in vivo" Class III antiarrhythmic activity.

The biological data is set forth in the table below.

| | Biological Data | | | | | | | | | |
|---|---|---|---|---|---|---|---|---|---|---|
| | Purkinje Fiber 3 $\mu$M | | | | Anesthetized Dog (5 mg/kg) | | | | | |
| | BCL = 300 | | BCL = 1000 | | BCL = 300 | | | | | |
| Example | $APD_{-60}$ | $V_{max}$ | $APD_{-60}$ | $V_{max}$ | AERP | VERP | ACT | VCT | HR | BP |
| 1 | 15 (n = 2) | $-19$ | 29 ± 6 (n = 3) | $-8 \pm 5$ | 69 ± 7 | 25 ± 3 (n = 3) | 16 ± 1 | $-7 \pm 9$ | $-33 \pm 1$ (n = 3) | $-33 \pm 9$ |
| 5 | 30 | 7 | 50 | 14 | 56 | 13 | 6 | 3 | $-15$ | $-25$ |
| 4 | 16 | $-12$ | 33 | $-17$ | 24 | 13 | $-4$ | 0 | $-14$ | $-16$ |

Based upon the activity profile elicited by the compounds of this invention in the above-described standard scientifically recognized test models, the compounds are established as antiarrhythmic agents useful in the treatment of cardiac arrhythmia and conditions characterized by coronary arteries vasospasm. For that purpose, the compounds may be administered orally or parenterally in suitable dosage forms compatible with the route of administration, whether oral, intraperitoneal, intramuscular, intravenous, intranasal, buccal, etc. The effective dose range determined in the animal test models has been established at from about 1 to about 5 milligrams per kilogram host body weight (preferably from 2 to 10 mg/kg) i.v., and from about 2 to about 10 mg/kg (preferably 5 to 20 mg/kg) p.o., to be administered in single or plural doses as needed to relieve the arrhythmatic dysfunction. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 50 milligrams to about 400 milligrams) of the active ingredient alone or in combination with adjuvants needed for conventional coating, tableting, solubilizing, flavoring or coloring. Parenteral administration with liquid unit dosage forms may be via sterile solutions or suspensions in aqueous or oleaginous medium. Isotonic aqueous vehicle for injection is preferred with or without stabilizers, preservatives and emulsifiers.

The following examples illustrate the preparation of a representative number of compounds of this invention.

EXAMPLE 1

α-[(4-Nitrophenoxy)methyl]-4-(2-pyridinyl)-1-piperazineethanol Dihydrochloride

Step (1) Preparation of 1-p-Nitrophenoxy-2,3-propene

To a solution of p-nitro sodiumphenoxide (30 g, 0.186 mol) in DMF (400 mL) was added allyl bromide (24 mL, 0.28 mol). The reaction mixture was stirred under a nitrogen atmosphere at room temperature for 48 hours, then diluted with water (300 mL) and extracted with ether (3×100 mL). The combined organic fraction was diluted with pentane until it became turbid. It was then washed with water (2×100 mL), dried (MgSO$_4$), and concentrated to afford 27.5 g of product (83%) as a red oil of sufficient purity to use in the next step.

$^1$H NMR (CDCl$_3$): δ 8.19 (d, 2H, J=8 Hz, ArH), 6.97 (d, 2H, J=8 Hz, ArH), 6.17 (m, 1H,—CH=CH$_2$),5.40 (m, 2H,—CH=CHH$_2$), 4.65 (d, 2H, J=6 Hz, O—CH$_2$—).

Step (2) Preparation of 1-p-Nitrophenoxy-2,3-propeneoxide

To a solution of 1-p-nitrophenoxy-2,3-propene (19.25 g, 0.107 mol) in dry methylene chloride (300 mL) was slowly added meta-chloroperbenzoic acid (24.13 g, 0.14 mol). The reaction mixture was stirred under a nitrogen atmosphere for 48 hours. The mixture was filtered and the filtrate was concentrated to afford a yellow residue. Trituration of the yellow residue with ether, yielded the crude product as yellow crystals. Purification by flash chromatography afforded 11.75 g (56%) of product as a light yellow solid, m.p. 63°–65° C.

$^1$H NMR (CDCl$_3$): δ 8.15 (d, J=8.2 HZ, 2 ArH), 6.95 (d, J=8.2 Hz, 2 ArH), 4.36 and 3.98 (2m,—OCH$_2$—CH), 3.36 (m, 1H, epoxide methine), 2.92 and 2.76 (2m, 2H, epoxide methylene)

Anal. Calcd.: C, 59.19; H, 5.87; N, 6.27. Found: C, 59.51; H, 5.84; N, 6.31.

Step (3) Preparation of α-[(4-Nitrophenoxy)methyl]-4-(2-pyridinyl)-1-piperazineethanol Dihydrochloride To a stirred solution of 1-p-nitrophenoxy-2,3-propeneoxide (4.00 g, 20.49 mmol) in acetonitrile (50 mL) was added 1-(2-pyridinyl)piperazine (6.24 mL, 40.98 mmol). The resulting mixture was stirred at reflux for 18 hours, cooled to 20° C., and filtered. The collected solid was treated with ethanolic HCl and ether to afford 6.10 g (69%) of analytically pure dihydrochloride salt as a white powder, m.p. 244°–246° C. (dec.).

$^1$H NMR (DMSO-D$_6$): δ 10.9 (m, 2H, N⊕H), 8.22 (d, J=9.21 Hz, 2H, ArH), 8.12 (dd, J$_1$=1.2 Hz, J$_2$=5.4 Hz, 1H, ArH), 7.87 (m, 1H, ArH), 7.21 (m, 1H, ArH), 7.17 (d, J=9.27 Hz, 2H ArH), 6.91 (t, J=6.19 Hz, 1H, ArH), 4.50–4.42 (m, 4e,uns/H/ , —OCH$_2$—CH—OH), 4.15 (brd, 2H, —CHOH—CH$_2$—N), 3.89–3.15 (brm, 8H, piperazine H's)

IR (KBr): cm$^{-1}$ 3320 (OH), 1600–1500 (NO$_2$).

MS (m/e): 358 (18%), 107 (100%).

Anal. Calcd.: C, 50.12; H, 5.61; N, 12.99. Found: C, 49.96; H, 5.67; N, 12.92.

EXAMPLE 2

(S)-α-[-(4-Nitrophenoxy)methyl]-4-(2-pyridinyl)-1-piperazine Ethanol Dihydrochloride

Step (1) Preparation of 2-(S)-1,2-Epoxy-3-(p-nitrophenoxy)propane

To a solution of sodium 4-nitrophenoxide (3.18 g, 19.74 mmol) in DMF (20 mL) at 0° C. was added 2-(S)(+)glycidyl-3-nitrobenzenesulfonate (4.00 g, 15.43 mmol). The mixture was stirred for 18 hours under N$_2$ at 20° C. The reaction mixture was diluted with brine (50 mL) and extracted with ethyl acetate. The combined organic phase was washed with cold 0.1N NaOH water, and brine. The extract was dried (MgSO$_4$) and concentrated to afford 3.0 g of product which was purified by flash column chromatography using 2:1 hexane/ethyl acetate to afford 2.49 g (83%) of product as a white solid, m.p. 73°–75° C.

$^1$H NMR (CDCl$_3$): δ 8.20 (d, J=9 Hz, 2H, ArH), 7.00 (d, J=9 Hz, 2H, ArH), 4.39 and 4.00 (2m, —OCH$_2$—CH), 3.38 (m, 1H, epoxide methine), 2.90 and 2.80 (2m, 2H, epoxide methylene)

[α]$_D^{25}$= +10.6° (MeOH).

Step (2) Preparation of (S)-α-[(4-Nitrophenoxy)methyl]-4-(2-pyridinyl)-1-piperazine Ethanol Dihydrochloride 1-(2-Pyridinyl)piperazine (1.56 mL, 10.26 mmol) was added to a stirred solution of 2-(S)-1,2-epoxy-3-(p-nitrophenoxy)propane (1.00 g, 5.13 mmol) in acetonitrile (15 mL). The resulting mixture was refluxed for 18 hours, cooled, and the precipitated solid was collected by filtration to afford 1.14 g (62%) of product. The material was treated with ethanolic HCl to afford its dihydrochloride salt which was recrystallized from ethanol/ether to afford 1.20 g of analytically pure product as a white solid m.p. 239°–240° C. (dec.) which was identical with the racemate except for rotation.

Anal. Calcd.: C, 50.12; H, 5.61; N, 12.99. Found: C, 49.82; H, 5.49; N, 12.62.

[α]$_D^{25}$= −5.88° (DMSO).

EXAMPLE 3

(R)-α-[(4-Nitrophenoxy)methyl]-4-(2-pyridinyl)-1-piperazine Ethanol Dihydrochloride

Step (1) Preparation of 2-(R)-1,2-Epoxy-3-(p-nitrophenoxy)propane

To a solution of sodium 4-nitrophenoxide (2.38 g, 13.30 mmol) in DMF (15 mL) at 0° C. was added 2-(R)(−)glycidyl-3-nitrobenzenesulfonate (3.00 g, 11.57 mmol). The mixture was stirred for 18 hours under N$_2$ at 20° C. The reaction mixture was worked up and purified as in Example 2, Step 1 to afford 1.83 g (81%) of epoxide as a white solid, m.p. 75°–76° C.

$^1$H NMR (CDCl$_3$): δ 8.20 (d, J=9 Hz, 2H, ArH), 7.00 (d, J=9 Hz, 2H, ArH), 4.39 and 4.00 (2m,—OCH$_2$—CH), 3.38 (m, 1H, epoxide methine), 2.90 and 2.79 (2m, 2H, epoxide methylene)

[α]$_D^{25}$= −11.0° (MeOH).

Step (2) Preparation of (R)-α-[(4-Nitrophenoxy)methyl]-4-(2-pyridinyl)-1-piperazine Ethanol Dihydrochloride 1-(2-Pyridinyl)piperazine (1.56 mL, 10.26 mmol) was added to a stirred solution of 2-(R)-1,2-epoxy-3-(p-nitrophenoxy)propane (1.00 g, 5.13 mmol) in acetonitrile (15 mL). The resulting mixture was refluxed for 18 hours, cooled, and the precipitated product was collected by filtration. Yield: 1.15 g (63%). The dihydrochloride salt was prepared by treatment with ethanolic HCl and was recrystallized from ethanol/ether to afford 1.20 g of analytically pure white solid, m.p. 242°-244° C. (dec.) which was identical with the racemate except for rotation.

Anal. Calcd.: C, 50.12; H, 5.61; N, 12.99. Found: C, 49.70; H, 5.53; N, 12.66.

$[\alpha]_D^{25} = +6.50°$ (DMSO).

EXAMPLE 4

N-[4-[2-Hydroxy-3-[4-(2-pyrimidinyl)-1-piperazinyl]propoxy]phenyl]methanesulfonamide

Step (1) Preparation of α-[(4-Nitrophenoxy)methyl]-4-(2-pyrimidinyl)-1-piperazineethanol Dihydrochloride 1-(2-Pyrimidinyl)piperazine (1.65 g, 10.06 mmol) and 1,2-epoxy-3-(p-nitrophenoxy)propane, prepared by the process of Example 1, Step 2, (1.31 g, 6.71 mmol) were refluxed in acetonitrile (30 mL) for 5 hours. The reaction was subsequently stirred at 25° C. for 24 hours, concentrated to dryness, and the resulting residue was triturated with ether/hexane to afford 1.57 g (62%) of product as a white solid which was taken on without further purification. A small amount was converted into its dihydrochloride salt for analysis.

$^1$H NMR (DMSO-D$_6$): δ 10.69 (br s, 2H, N$^\oplus$H), 8.44 (d, J=4.67 Hz, 2H, ArH), 8.22 (d, J=9.27 Hz, 2H, ArH), 7.17 (d, J=9.26 Hz, 2H, ArH), 6.76 (m, 1H, ArH), 4.85 (br m, 1H, —OH), 4.66 (m, 2H, —OCH$_2$—CHOH), 4.49 (m, 1H, OCH$_2$—CHOH), 4.15 (br d, 2H, CH$_2$N), 3.70-3.10 (br m, 8H, piperazine H's)

IR (KBr, cm$^{-1}$): 3300 (OH).

MS (m/e): 359 (M$^\oplus$, 60%), 177 (100%).

Step (2) Preparation of α-[(4-Aminophenoxy)methyl]-4-(2-pyrimidinyl)-1-piperazineethanol α-[(4-Nitrophenoxy)methyl]-4-(2-pyrimidinyl)-1-piperazineethanol dihydrochloride (1.32 g, 3.68 mmol) was hydrogenated in a Parr reactor using 5% Pd/C (0.198 g, 15% by wt) in ethyl acetate (40 mL). After 5 hours, the mixture was filtered through solka floc and the filtrate was concentrated to afford 1.2 g (100%) of product as a pale oil of sufficient purity for use in the next step.

$^1$H NMR (CDCl$_3$): δ 8.25 (d, J=5.4 Hz, 2H, ArH), 6.72 (d, J=9.0 Hz, 2H, ArH), 6.59 (d, J=9.2 Hz, 2H, ArH), 6.45 (m, 1H, ArH), 4.10 (m, 1H, —CHOH), 3.90 -3.50 (m, 9H, OCH$_2$-CHOH, NH$_2$, 4 piperazine CH$_2$), 2.80-2.40 (m, 6H, CH$_2$—N, 4 piperazine CH$_2$).

Step (3) Preparation of N-[4-[2-Hydroxy-3-[4-(2-pyrimidinyl)-1-piperazinyl]propoxy]phenyl]methanesulfonamide Methanesulfonyl chloride (0.31 mL, 4.01 mmol) was added dropwise to a stirred solution of α-[(4-aminophenoxy)methyl]-4-(2-pyrimidinyl)-1-piperazineethanol (1.20 g, 3.65 mmol) in pyridine (15 mL) at −30° C. under N$_2$. The reaction was stirred at 25° C. for 1.5 hours. Ice water was added, and the resulting mixture was extracted with ethyl acetate. The organic phase was dried (MgSO$_4$), decolorized (charcoal), and concentrated to afford a residue. Trituration followed by recrystallization from methanol/ethyl acetate/hexane afforded 0.65 g (44%) of analytically pure product, m.p. 143°-146° C. as a tan solid.

$^1$H NMR (DMSO-D$_6$): δ 9.35 (s, 1H, CH$_3$SO$_2$NH), 8.35 (d, J=4.77 Hz, 2H, ArH), 7.15 (d, J=8.72 Hz, 2H, ArH), 6.93 (d, J=8.72 Hz, 2H, ArH), 6.61 (m, 1H, ArH), 4.92 (m, 1H, OH), 3.98 (m, 2H, OCH$_2$ CHOH), 3.87 (m, 1H, OCH$_2$CHOH), 3.71 (m, 4H, piperazine CH$_2$), 2.88 (s, 3H, CH$_3$SO$_2$NH), 2.49 (m, 6H, CH$_2$N and piperazine CH$_2$)

IR (KBr, cm$^{-1}$): 3120 (OH).

MS (m/e): 407 (M$^\oplus$, 10%), 177 (100%).

Anal. Calcd.: C, 53.06; H, 6.18; N, 17.19. Found: C, 52.81; H, 5.84; N, 16.84.

EXAMPLE 5

N-[4-[2-Hydroxy-3-[4-(2-pyridinyl)-1-piperazinyl]propoxy]phenyl]methanesulfonamide

Step (1) Preparation of 3-[(4-Amino)phenoxy]-1-propene

To 3-[(4-nitro)phenoxy]-1-propene prepared by the process of Example 1, Step 1, (12.65 g, 70.67 mmol) in concentrated HCl (85 mL) at 0° C. was slowly added stannous chloride (48 g, 212 mmol). After stirring for 20 minutes at 55° C., the mixture was cooled to 0° C. and carefully basified with 50% NaOH. The cloudy mixture was extracted with ether. The organic phase was decolorized (charcoal), dried (MgSO$_4$), and concentrated to afford product (8.50 g, 81%) as a yellow oil which was used directly in the next step.

$^1$H NMR (CDCl$_3$): δ 7.05 (m, 4H, ArH), 6.4 (m, 1H, OCH$_2$—CH=CH$_2$), 5.70 (m, 2H, CH$_2$CH=CH$_2$), 4.80 (d, 2H, OCH$_2$CH=CH$_2$).

Step (2) Preparation of N-[4-(2-Propeneoxy)phenyl]methanesulfonamide

Methanesulfonyl chloride (5.06 mL, 65.32 mmol) was added to a stirred solution of 3-[(4-amino)phenoxy]-1-propene (8.11 g, 54.43 mmol) in pyridine (80 mL) at 0° C. The mixture was stirred for 72 hours and was then poured slowly into ice-water and extracted with ether. The organic phase was washed with cold 1N HCl and was then extracted with 1N NaOH solution. The aqueous phase was acidified and the product (9.05 g, 73%) precipitated out as a white solid.

$^1$H NMR (CDCl$_3$): δ 7.18 (d, J=6.75 Hz, 2H ArH), 6.88 (d, J=8.94 Hz, 2H ArH), 6.00 (m, 1H, CH$_2$CH=CH$_2$), 5.40 and 5.30 (2m, OCH=CH$_2$), 4.50 (m, OCH$_2$CH=CH$_2$).

Anal. Calcd.: C,52.85; H,5.76; N,6.16.

Found: C,52.80; H,5.63; N,5.99.

Step (3) Preparation of 1-[(4-Methanesulfonamido)phenoxy]-2,3-propeneoxide m-Chloroperoxybenzoic acid (12.16 g, 70.48 mmol) was added to a solution of N-[4-(2-propeneoxy)phenyl]methanesulfonamide (8.00 g, 35.24 mmol) in methylene chloride (120 mL). The mixture was stirred overnight at reflux, cooled, and filtered. Concentration afforded crude product which was purified by flash chromatography using 1:1 hexane/ethyl acetate. Yield 5.55 g (65%) of white solid.

¹H NMR (CDCl₃): δ 7.17 (d, J=6.87 Hz, 2H ArH), 6.90 (d, J=8.93 Hz, 2H, ArH), 6.40 (br s, NHSO₂CH₃), 4.20 (dd, J₁=5.54 Hz, J₂=2.98 Hz, 1H, epoxide CH₂), 3.90 (dd, H₁=5.54, J₂=5.78 Hz, 1H, epoxide CH₂), 3.35 (m, 1H, epoxide CH), 2.94 (s, 3H, NHSO₂CH₃), 2.90 and 2.76 (2m, OCH₂).

IR (KBr): 3240 (NH).

MS (m/e): 243 (60% M+), 164 (100%).

Step (4) Preparation of
N-[4-[2-Hydroxy-3-[4-(2-pyridinyl)-1-piperazinyl]-propoxy]phenyl]methanesulfonamide To a stirred solution of 1,2-epoxy-3-(p-methanesulfonamidophenoxy)propane (2.00 g, 8.22 mmol) in acetonitrile (18 mL) was added 1-(2-pyridinyl)piperazine (2.50 mL, 16.44 mmol) and the resulting mixture was refluxed for 18 hours. Upon cooling, 1:1 hexane/ether (30 mL) was added and the resulting mixture was filtered. The collected product was continually triturated with ether and then dried overnight in vacuo to afford 2.19 g (66%) of analytically pure product as an off-white solid, m.p. 131°-132° C.

¹H NMR (DMSO-D₆): δ 9.33 (br s, 1H,—NHSO₂CH₃), 8.08 (m, 1H, ArH), 7.50 (m, 1H, ArH), 7.13 (d, J=8.91 Hz, 2H, ArH), 6.92 (d, J=9.01 Hz, 2H, ArH), 6.78 (d, J=8.62, 1H, ArH), 6.61 (m, 1H, ArH), 4.89 (br d, J=4.12 Hz, 1H, —OH), 3.95 (m, 2H, —OCH₂CHOH), 3.85 (m, 1H, —OCH₂ CHOH), 3.44-3.30 (m, 10H, CH₂N), 2.86 (s, 3H, —NH SO₂CH₃)

IR (KBr, cm⁻¹): 3200 (OH).

MS (m/e): 407 (MH⊕, 40%).

Anal. Calcd.: C, 56.14; H, 6.45; N, 13.78.
Found: C, 55.90; H, 6.56; N, 13.93.

We claim:

1. The compounds of formula (I)

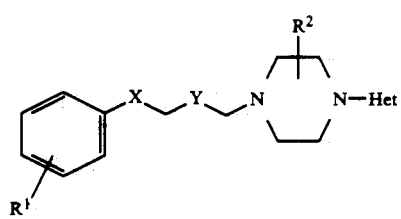

wherein R¹ is alkylsulfonamido of 1 to 6 carbons, arylsulfonamido of 6 to 10 carbons, perfluoroalkylsulfonamido of 1 to 6 carbon atoms, alkylsulfone or alkylsulfoxide of 1 to 6 carbon atoms, NO₂, CN, or 1-imidazolyl; R² is hydrogen or straight or branched alkyl chain of 1 to 6 carbon atoms; X is O, S, or NR³ wherein R³ is H or a straight or branched alkyl chain of 1 to 6 carbon atoms; Y is CH₂ or CHOH; Het is selected from the group consisting of

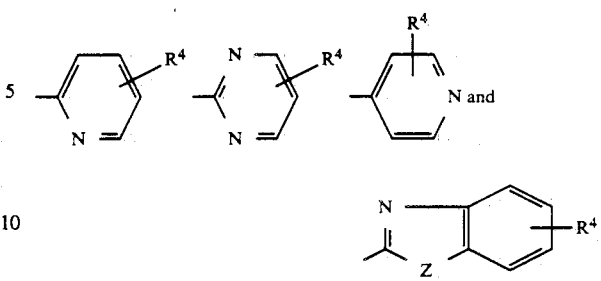

wherein R⁴ is H, —NHSO₂ (C₁ to C₆ alkyl) or NO₂ and Z is O, S, NR⁵ wherein R⁵ is H or alkyl of 1 to 6 carbon atoms and the pharmaceutically acceptable salts thereof.

2. The compounds according to claim 1 of formula (II)

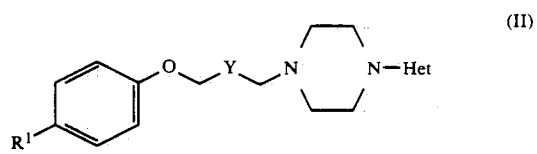

wherein R¹ is methylsulfonamido, or nitro; Y is CH₂ or CHOH; Het is selected from the group consisting of

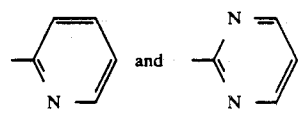

and the pharmaceutically acceptable salts thereof.

3. The compound according to claim 2 α[(4-nitrophenoxy)methyl]-4-(2-pyridinyl)-1-piperazineethanol and the pharmaceutically acceptable salts thereof.

4. The compound according to claim 2 N-[4-[2-hydroxy-3-[4-(2-pyridinyl)-1-piperazinyl]pro-poxy]-phenyl]methanesulfonamide and the pharmaceutically acceptable salts thereof.

5. The compound according to claim 2 N-[4-[2-hydroxy-3-[4-(2-pyrimidinyl)-1-piperazinyl]propoxy]-methanesulfonamide and the pharmaceutically acceptable salts thereof.

6. The compound according to claim 2 (S)-α-[(4-nitrophenoxy)methyl]-4-(2-pyridinyl)-1-piperazineethanol and the pharmaceutically acceptable salts thereof.

7. The compound according to claim 2 (R)-α-[(4-nitrophenoxy)methyl]-4-(2-pyridinyl)-1-piperazineethanol and the pharmaceutically acceptable salts thereof.

8. A pharmaceutical composition having antiarrhythmic properties which comprises an effective amount of a compound of the formula (I) of claim 1 or its physiologically tolerated acid addition salt and a pharmaceutically acceptable carrier and/or diluent.

9. A method of treating arrhythmia which comprises administering an effective amount of a compound of the formula (I) of claim 1 or its pharmaceutically acceptable acid addition salt.

* * * * *